United States Patent
Debenham

(10) Patent No.: US 6,909,019 B1
(45) Date of Patent: Jun. 21, 2005

(54) PROCESS FOR PREPARING ALDEHYDES

(75) Inventor: Sheryl Davis Debenham, Scotch Plains, NJ (US)

(73) Assignee: Eastman Chemical Company, Kingsport, TN (US)

(*) Notice: Subject to any disclaimer, the term of this patent is extended or adjusted under 35 U.S.C. 154(b) by 10 days.

(21) Appl. No.: 10/853,607

(22) Filed: May 25, 2004

(51) Int. Cl.$^7$ .............................................. C07C 45/51
(52) U.S. Cl. ...................... 568/426; 568/427; 568/450; 568/485; 568/487; 568/489; 568/491
(58) Field of Search ................................ 568/426, 427, 568/450, 485, 489, 491

(56) References Cited

U.S. PATENT DOCUMENTS

| | | | |
|---|---|---|---|
| 4,742,178 A | 5/1988 | Nelson et al. | |
| 4,774,362 A | 9/1988 | Devon et al. | |
| 4,845,306 A | 7/1989 | Puckette | |
| 4,871,878 A | 10/1989 | Puckette et al. | |
| 4,950,797 A | * 8/1990 | Kummer et al. | ............ 568/450 |
| 4,960,949 A | 10/1990 | Devon et al. | |

FOREIGN PATENT DOCUMENTS

WO     WO 00/18361     4/2000

OTHER PUBLICATIONS

Larock et al. Synthesis of Aryl–Substituted Aldehydes and Ketones Via Palladium– Catalyzed Coupling of Aryl Halides and Non–Allylic Unsaturated Alcohols. Tetrahedron Letters; 1989, vol. 30 (48), p 6629–6632.*

Trost et al. Tetrahedron Letters;1992, vol. 32 (26) p 3039–3042.*

Sasson et al. Tetrahedron Letters; 1974, p 4133–4136.*

Chalk et al. Palladium–Catalyzed Vinyl Substitution Reactions. II. Synethesis of Aryl Substituted Allylic Alcohols, Aldehydes, and Ketones from Aryl Halides and Unsaturated Alcohols. □□ Journal of Organic Chemistry; 1976, vol. 41 (7), p 1206–1209.*

Davies, Organotransition Metal Chemistry: Applications to Organic Synthesis, Pergamon Press, Oxford, 1982, pp. 282–284.

Strohmeier et al., Journal of Organometallic Chemistry, 1975, vol. 86, C17–C19.

March, Journal of Advanced Organic Chemistry, $3^{rd}$ Ed., John Wiley & Sons, New York, 1985, pp. 655–656.

Melpolder et al., Journal of Organic Chemistry, 1976, vol. 41, No. 2, pp. 265–272.

Journal of American Chemical Society, vol. 85, pp. 1549–1550.

* cited by examiner

*Primary Examiner*—Johann Richter
*Assistant Examiner*—Sikarl A. Witherspoon
(74) *Attorney, Agent, or Firm*—Michael J. Blake; Bernard J. Graves, Jr.

(57) ABSTRACT

A process is disclosed for preparing aldehydes by isomerization of the corresponding unsaturated primary alcohols using a transition metal catalyst system, in an alcoholic solvent and in the presence of an acid. An aldehyde forms by isomerizing an unsaturated primary alcohol under conditions that protect the newly formed aldehyde as a dialkylacetal in situ during the reaction. Protecting the aldehyde as an acetal allows for facile separation of the product from the catalyst as well as effectively driving the reaction toward completion.

15 Claims, No Drawings

PROCESS FOR PREPARING ALDEHYDES

FIELD OF THE INVENTION

This invention pertains to a process for preparing aldehydes. More specifically, the present invention pertains to preparing an aldehyde by isomerizing an unsaturated primary alcohol.

BACKGROUND OF THE INVENTION

Production of aldehydes by transition-metal catalyzed isomerization of unsaturated alcohols is well known. For example, allyl alcohol and methallyl alcohol isomerize to proprionaldehyde and isobutyraldehyde in the presence of metal complexes. (Davies, S. G. in *Organotransition Metal Chemistry: Applications to Organic Synthesis*, Pergamon, Oxford, 1982, 282–284.) However, the transformation often provides a complex reaction mixture having significant amounts of byproducts, thus complicating attempts to purify the desired aldehyde. Fortuitous selection of catalyst and solvent, on the other hand, can provide complete conversion to the desired aldehyde. One example involves the use of RuHCl(PPh$_3$)$_3$ to isomerize aliphatic allyl alcohols, which provides excellent conversion of secondary alcohols to ketones. The catalyst fails, however, to produce aldehydes from primary alcohols; no reaction occurs. (Sasson et al., *Tetrahedron Lett.*, 1974, 4133–4136.)

In another example, isobutenol is completely isomerized to isobutyraldehyde upon treatment with RhHCO(PPh$_3$)$_3$ in trifluoroethanol at 70° C. in three hours. The foregoing reaction is solvent and catalyst dependent, however, and conversion drops to less than 70% when a ruthenium or copper catalyst is used or when the expensive trifluoroethanol is not used. Further, a method to separate the homogenous catalyst from the reaction product is not reported. (Strohmeier et al., *J. Organometallic Chem.*, 1975, 86, C17–C19.) Trost reports the use of Cp(Ph$_3$P)$_2$RuCl (Cp=cyclopentadienyl) for the isomerization of allyl alcohols to aldehydes or ketones although conversion ranges from 31–92% depending on the substrate; separation of the product from the catalyst is conducted by expensive silica gel chromatography. (Trost et al., *Tetrahedron Lett.*, 1991, 32, 3039–3042.)

Prior methods also reveal separation problems even if a reaction produces the target aldehyde. Since most rhodium complexes and some ruthenium complexes are also excellent decarbonylation catalysts, separation of the aldehyde from the catalyst by distillation is almost impossible due to decomposition of the aldehyde to form the decarbonylated product. (March, J. *Advanced Organic Chemistry*, 3$^{rd}$ Ed., John Wiley & Sons, New York, 1985, 655–656 and references therein.) Additional side reactions can include aldol condensation of the aldehyde products.

A method used to separate an aldehyde synthesized by isomerizing an allyl alcohol by contacting it with a molten phosphineirhodium reaction medium involves passing a carrier gas through the reaction mixture. (See, U.S. Pat. No. 4,950,797.) The vaporized carbonyl compound is removed from the emergent gas mixture by cooling. However, this method is limited to low-boiling aliphatic aldehydes since the boiling point of the product must be less than the temperature of the molten reaction mixture (180° C. at 1 atmosphere).

As mentioned above, problems encountered during the isomerization of allylic alcohols (e.g., to propionaldehyde) include the incomplete reaction and formation of byproducts. This complex mixture can be especially troublesome in the case of aryl-substituted allylic alcohols in which case equilibrium is established between the aldehyde and the aryl-conjugated unsaturated alcohol. As a result, the isomerization of 4-aryl-buten-1-ols to the corresponding aldehydes has not been reported in the literature.

Aryl-substituted aldehydes can be prepared by Heck addition of iodo- or bromo-benzene to unsaturated alcohols in the presence of a palladium catalyst, base and, in some cases, a phosphine ligand. (Chalk et al., *J. Org. Chem.*, 1976, 41, 1206–1208; Melpolder et al., *J. Org. Chem.*, 1976, 41, 265–272.) However, these palladium-catalyzed additions result in the production of a mixture of linear and branched addition products. In the case of 4-penten-1-ol, addition of aryl iodide resulted in improved ratios of the 5- to 4-arylation products (83:17) but required the use of stoichiometric amounts of additives (Bu$_4$NCl, LiOAc, LiCl, DMF) and increased reaction time of 4 days. (Larock et al., *Tetrahedron Lett.*, 1989, 30, 6629–6632.) Due to the complexity of the reaction mixtures, this type of process has not found use in industrial applications.

BRIEF SUMMARY OF THE INVENTION

The present invention provides process for the preparation of an aldehyde comprising the steps of:

(1) heating a reaction mixture comprising a β,γ-ethylenically-unsaturated primary alcohol, an alkanol, an acid, and a catalyst complex comprising at least one transition metal selected from ruthenium, rhodium, iridium, palladium, platinum, cobalt and iron to form a dialkylacetal of the aldehyde corresponding to the alcohol;

(2) adding a base to the reaction mixture of step (1);

(3) purifying the mixture resulting from step (2) to obtain a product comprising the dialkylacetal; and (4) contacting the product obtained in step (3) with an acid and water to obtain an aldehyde corresponding to the dialkylacetal.

Performing the isomerization in the presence of an alkanol and acid in step (1) produces a dialkylacetal of the aldehyde that allows for improved conversion of the unsaturated alcohol to the intended aldehyde. The dialkylacetal can be separated, e.g., by distillation, from the catalyst-containing reaction mixture while avoiding unwanted side reactions, such as decarbonylation or condensation, that may occur if the initial product is the aldehyde. The dialkylacetal may be converted to the aldehyde by addition of water and an acid.

DETAILED DESCRIPTION

The β,γ-ethylenically-unsaturated primary alcohol reactant employed in the present invention contains at least 3 carbons, preferably from about 3 to about 30 carbon atoms. Examples of the alcohol reactants include compounds having the formula I:

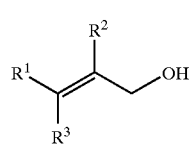

wherein R$^1$, R$^2$ and R$^3$ are independently selected from hydrogen, C$_1$–C$_{20}$ alkyl, C$_6$–C$_{20}$ aryl, or C$_4$–C$_{20}$ heteroaryl groups. The alkyl, aryl and heteroaryl groups may be unsubstituted or substituted with up to three substituents such as alkoxy, alkylthio, hydroxy, alkanoyloxy, halogen (e.g., Br, Cl or I), nitro and cyano. The heteroatoms of the heteroaryl group may be oxygen, sulfur and/or nitrogen; the heteroaryl group may contain from 1 up to 3 heteroatoms. The preferred unsaturated primary alcohols for use herein have formula I wherein $R^1$ and $R^2$ and $R^3$ are independently selected from hydrogen, $C_1$–$C_6$ substituted or unsubstituted alkyl, $C_6$–$C_{10}$ substituted or unsubstituted aryl, or $C_4$–$C_{10}$ substituted or unsubstituted heteroaryl. In each of the foregoing instances, the alkyl group may be straight or branched chain. The process is especially useful for converting 4-phenyl-2-buten-1-ol($R^1$=$CH_2C_6H_5$, $R^2$=$R^3$=H) to 4-phenyl-1-butyraldehyde through the 4-phenyl-1,1-dialkoxybutane intermediate (e.g., when using ethanol, the corresponding diethoxybutane intermediate forms).

The skilled artisan will understand that each of the references herein to groups or moieties having a stated range of carbon atoms, such as "$C_1$–$C_6$-alkyl," includes not only the $C_1$ group (methyl) and $C_6$ group (hexyl) end points, but also each of the corresponding individual $C_2$, $C_3$, $C_4$ and $C_5$ groups. In addition, it will be understood that each of the individual points within a stated range of carbon atoms may be further combined to describe subranges that are inherently within the stated overall range. For example, the term "$C_1$–$C_6$-alkyl" includes not only the individual moieties $C_1$ through $C_6$, but also contemplates subranges such as "$C_2$–C5-alkyl."

The process in step (1) is carried out in the presence of an alkanol that functions both as the process solvent and as an auxiliary or secondary reactant to form the above-described dialkylacetal. The alkanol may be described by the formula $R^4OH$; $R^4$ is $C_1$–$C_6$ straight or branched chain alkyl, and may optionally be substituted with hydroxyl when $R^4$ is $C_2$ or greater. The alkanol preferably contains 1 to 3 carbon atoms (e.g., methanol, ethanol or iso- or n-propanol). Some or all of the alkanol may be employed in the form of an alkylene glycol such as ethylene glycol ($R^4$ is $HOCH_2CH_2$—) or propylene glycol ($R^4$ is $HOCH_2CH_2CH_2$— or $CH_3CHOHCH$—). The amount of alkanol and/or alkylene glycol employed typically is an amount that provides an alkanol/glycol to β,γ-ethylenically-unsaturated primary alcohol reactant weight ratio of about 3:1 to 50:1.

The transition metal complex catalyst employed in step (1) should be soluble in the alkanol and comprises at least one transition metal selected from ruthenium, rhodium, iridium, palladium, platinum, cobalt and iron. The metal is preferably ruthenium or rhodium. The transition metals preferably are used in combination with a phosphine. The components of the catalyst system may be provided either as a preformed complex of the transition metal or as separate components. Examples of preformed complexes containing, for example, rhodium and ruthenium, have the general formula IV:

$$\text{MetH}_m[\text{CO}]_n X_p Y_q \qquad \qquad \text{IV}$$

wherein Met is a transition metal, X is a halogen atom such as chloro, bromo or iodo, Y is a tertiary (trisubstituted) phosphine molecule, m is 0 to 3, n is 0 to 5, p is 0 to 4, and q is 1 to 4 and the sum of m+n+p+q is 4 to 6.

Examples of phosphine ligands that Y may represent include tributylphosphine, butyldiphenylphosphine, tribenzylphosphine, tricyclohexylphosphine, 1,2-bis(diphenylphosphino)ethane, 1,3-bis(diphenylphosphino)propane, 2,2'-bis(diphenylphosphino methyl)-1,1'-biphenyl, and 1,2-bis(diphenylphosphinomethyl)benzene. Further examples of tertiary phosphines are disclosed in, e.g., U.S. Pat. Nos. 4,845,306, 4,742,178, 4,774,362, 4,871,878 and 4,960,949. Typical phosphine ligands may be represented by the general formula:

wherein $R^5$, $R^6$ and $R^7$ are the same or different and each is a hydrocarbyl containing from 1 up to about 12 carbon atoms and $R^8$ is a hydrocarbylene group linking the 2 phosphorus atoms through a chain of 2 to 8 carbon atoms. Examples of the hydrocarbyl groups that $R^5$, $R^6$ and $R^7$ may represent include alkyl including aryl-substituted alkyl such as benzyl, cycloalkyl such as cyclohexyl, and aryl such as phenyl and phenyl substituted with one or more alkyl groups. Examples of hydrocarbylene groups that $R^8$ may represent include alkylene groups such as ethylene, trimethylene and hexamethylene, cycloalkylene such as cyclohexylene, and phenylene, naphthalene and biphenylene.

The following are examples of suitable, preformed catalytic systems: dihydridotetrakis(triphenylphosphine)ruthenium ($RuH_2(Ph_3P)_4$), carbonylchlorohydridotris(triphenylphosphine)ruthenium ($RuClH(CO)(Ph_3P)_3$), chlorohydridotris(triphenylphosphine)ruthenium ($RuHCl(Ph_3P)_3$), dichlorotris(triphenylphosphine)ruthenium ($RuCl_2(Ph_3P)_3$), chlorotris(triphenylphosphine)rhodium ($RhCl(Ph_3P)_3$), and hydridocarbonyltris(triphenylphosphine)rhodium ($RhH(CO)(Ph_3P)_3$).

The tertiary phosphine and transition metal components of the catalyst complex may be provided to the isomerization process (i.e., the reaction mixture) as separate components, provided that at least 1 mole of tertiary phosphine is used per gram-atom of transition metal. Examples of tertiary phosphine compounds that may be used are set forth above. The form in which the transition metal catalyst component is provided is, in general, not critical to the operation of the isomerization process. For example, rhodium or ruthenium may be supplied in the form of their halides, carbonyl halides or carbonylacetylacetonates. Larger amounts of tertiary phosphine compound, amounts which give a mole phosphine:gram Met of up to 10, may be used and may be advantageous depending on the particular form in which the rhodium or ruthenium is provided to the catalyst system.

The catalytically effective amount of the isomerization catalyst is in the range of about 0.001 to about 10 gram atoms of transition metal per mole of β,γ-ethylenically-unsaturated primary alcohol, and preferably about 0.01 to about 0.05 gram atoms of transition metal per mole of β,γ-ethylenically-unsaturated primary alcohol, initially present.

The presence of an acid in the reaction mixture facilitates formation of the acetal in step (1). The acid involved in the production of the dialkylacetal may be any acid that dissolves in the reaction mixture. Examples of such acids include inorganic acids such as hydrochloric acid, sulfuric acid, and phosphoric acids as well as strong organic acids such as trifluoroacetic acid, and alkyl- and aryl-sulfonic acids such as methanesulfonic acid, benzenesulfonic acid and toluenesulfonic acid. A preferred embodiment utilizes toluenesulfonic acid, benzenesulfonic acid, or methanesulfonic acid. The amount of acid can vary from about 0.1 to about 30 mole percent, preferably about 2 to about 8 mole percent, especially about 5 mole percent, based on the moles of β,γ-ethylenically-unsaturated primary alcohol initially present.

The dialkylacetal obtained from the first step of the process has the general formula II:

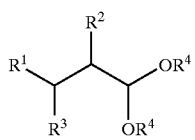

II wherein $R^1$, $R^2$ and $R^3$ are defined above; and each $R^4$ is alkyl or the two $R^4$ substituents may in combination represent an alkylene radical such as ethylene and methyl-substituted ethylene. Each $R^4$ preferably represents alkyl of 1 to 3 carbon atoms.

Step (1) of the isomerization process of the present invention is carried out at elevated temperatures, typically in the range of about 60° to about 120° C., preferably in the range of about 75° to about 100° C. Pressure is not an important feature of step (1) of the process and thus may be carried out at pressures slightly above or below atmospheric pressure. Step (1) may be operated until the majority of the unsaturated alcohol is converted to product, which depends on the amount of alcohol, catalyst and temperature used.

Following completion of step (1), wherein the dialkylacetal is formed, a base is added in accordance with step (2) to neutralize the acid present during step (1). The base may be any compound with a pKa higher than that of the acid employed in step (1). The base preferably is an inorganic base such as the hydroxides, carbonates and bicarbonates of the alkali metals and alkaline earth metals, e.g., the hydroxides, carbonates and bicarbonates of lithium, sodium, potassium, cesium, magnesium, calcium, and barium. A preferred embodiment utilizes sodium hydroxide or potassium hydroxide. The amount of base added in step (2) typically is about 1 to 10 equivalents of base per equivalent of acid used in step (1). Temperature is not an important feature of step (2), which may be carried out over a temperature range of about 0° about 50° C.

In step (3), the mixture resulting from step (2) is purified by means known to those in the art to obtain a product comprising the dialkylacetal of the aldehyde corresponding to the unsaturated primary alcohol from the reaction mixture of step (1). The purifying step uses conventional procedures such as, for example, crystallizing, distilling, or extracting.

The purified product comprising the dialkylacetal obtained from step (3) is contacted with an acid and water in step (4) to convert dialkylacetal of general formula II to an aldehyde having general formula III:

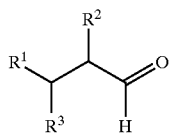

III wherein $R^1$, $R^2$ and $R^3$ are as defined above.

The acid for use in step (4) is a protic acid with a pKa of 5 or below and may, where appropriate, be the same or a different acid than was employed in step (1). Examples of such acids include inorganic acids such as hydrochloric acid, sulfuric acid, and phosphoric acids, organic acids including formic acid, acetic acid, propionic acid, butyric acid, or trifliuroacetic acid, and alkyl- and aryl-sulfonic acids such as methanesulfonic acid, benzenesulfonic acid and toluenesulfonic acid.

The amount of acid used in step (4) can be from about 0.1 equivalents to about 1000 equivalents based on compound II. In a preferred embodiment of the invention, the acid is a weak protic acid that is also used as a solvent for the step (4) reaction. Such weak protic acids are preferably chosen from $C_1$–$C_4$ alkanoic acids, most preferably acetic acid. The temperature of the reaction is such that the hydrolysis will occur in a facile manner, and can be from 0° C. to the boiling point of the reaction mixture.

The process provided by the present invention is further illustrated by the following example.

EXAMPLE

4-Phenyl-1,1-Diethoxybutane A 500 mL flask charged with 4-phenyl-2-buten-1-ol (17.26 g, 0.117 mol), ethanol (0.7 M, 167 mL) and p-toluenesulfonic acid (0.04 eq, 890 mg) was degassed with argon for 20 minutes. A catalyst consisting of H(CO)Rh(PPh$_3$)$_3$ (2 mol %, 2.2 g) was added to the flask and the mixture was heated at reflux for 72 hours. The reaction was cooled to 250° C. and NaOH (0.1 eq, 470 mg) was added. Ethanol was removed by distillation at atmospheric pressure. The material remaining was then distilled through a 14" Vigreux column at 0.1 torr. The dialkylacetal was recovered as a colorless oil (15.54 g, 60% yield, bp=83° C./01 torr). GC analysis (Cyclosil-B [J&W Scientific] 175° C., 8 psi, He carrier, $t_R$=18.5 min). $^1$H NMR (300 MHz, CDCl$_3$) δ 5 7.26–7.11 (m, 5H), 4.49–4.45 (m, 1H), 3.67–3.55 (m, 2H), 3.50–3.39 (m, 2H), 2.63–2.59 (t, J=6.6 Hz, 2H), 1.71–1.61 (m, 4H), 1.20–1.15 (m, 6H). $^{13}$C NMR (75 MHz, CDCl$_3$) δ 131.9, 128.3, 128.0, 125.5, 102.5, 60.6, 35.4, 32.9, 26.4, 15.1.

4-Phenyl-1-Butyraldeyde A mixture of 4-phenyl-1,1-diethoxybutane (15.54 g, 70.2 mmol), acetic acid (50 mL) and water (50 mL) were heated to reflux for 1 hour in a 200 mL flask. Water and acetic acid were removed by distillation at ambient pressure. The remaining residue was distilled through a 10" Vigreux column at 0.2 torr to provide the product as a colorless oil (8.3 g, 80% yield). GC analysis (Cyclosil-B [J&W Scientific] 175° C., 8 psi, He carrier, $t_R$=15.78 min). bp 55° C./0.20 mm Hg; $^1$H NMR (300 MHz, CDCl$_3$) δ 9.70 (s, $_1$ H); 7.32–7.14 (m, 5H); 2.65–2.60 (t, J=7.8 Hz, 2H); 2.42–2.38 (t, J=7.5 Hz, 2H); 1.97–1.88 (m, 2H). $^{13}$C NMR (75 MHz, CDCl$_3$ δ 202.1, 128.3, 126.0, 43.0, 34.9, 23.5.

The invention has been described in detail with particular reference to preferred embodiments thereof, but it will be understood that variations and modifications can be effected within the spirit and scope of the invention.

I claim:

1. A process for preparing an aldehyde comprising the steps of:
   (1) heating a reaction mixture comprising a β,γ-ethylenically-unsaturated primary alcohol, an alkanol, an acid, and a catalyst complex comprising at least one transition metal selected from ruthenium, rhodium, iridium, palladium, platinum, cobalt and iron, to obtain a dialkylacetal of the aldehyde corresponding to the alcohol;
   (2) adding a base to the reaction mixture of step (1);

(3) purifying the mixture resulting from step (2) to obtain a product comprising the dialkylacetal; and (4) contacting the product obtained in step (3) with an acid and water to obtain an aldehyde corresponding to the dialkylacetal.

2. A process according to claim 1 wherein catalyst complex comprises at least one transition metal selected from ruthenium and rhodium, and a phosphine having the formula:

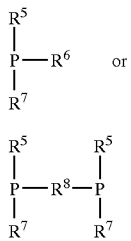

wherein $R^5$, $R^6$ and $R^7$ are the same or different and each is hydrocarbyl containing from 1 up to about 12 carbon atoms and $R^8$ is a hydrocarbylene linking group of 2 to 8 carbon atoms.

3. A process according to claim 2 wherein the acid in step (1) is hydrochloric acid, sulfuric acid, a phosphoric acid, trifluoroacetic acid, or an alkyl- or aryl-sulfonic acid.

4. A process according to claim 2 wherein the alkanol has 1 to 3 carbon atoms and the amount of alkanol employed provides an alkanol:β,γ-ethylenically-unsaturated primary alcohol reactant weight ratio of about 3:1 to 50:1.

5. A process according to claim 1 wherein step (3) comprises distilling, crystallizing, or extracting.

6. A process according to claim 1 wherein the transition metal is ruthenium or rhodium; the acid in step (1) is hydrochloric acid, sulfuric acid, a phosphoric acid, trifluoroacetic acid, or an alkyl- or aryl-sulfonic acid; the base used in step (2) is sodium hydroxide or potassium hydroxide; step (3) is carried out by distilling; and the acid in step (4) is acetic acid.

7. A process according to claim 1 wherein the catalyst complex comprises at least one transition metal selected from ruthenium and rhodium, and a phosphine having the formula:

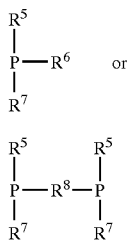

wherein $R^5$, $R^6$ and $R^7$ are the same or different and each is hydrocarbyl containing from 1 up to about 12 carbon atoms and $R^8$ is a hydrocarbylene linking group of 2 to 8 carbon atoms; the acid of step (1) is hydrochloric acid, sulfuric acid, a phosphoric acid, trifluoroacetic acid, or an alkyl- or aryl-sulfonic acid; the alkanol has 1 to 3 carbon atoms and the amount of alkanol employed provides an alkanol: β,γ-ethylenically-unsaturated primary alcohol reactant weight ratio of about 3:1 to 50:1; and the acid employed in step (4) is acetic acid.

8. A process according to claim 7 wherein the acid in step (1) is toluenesulfonic acid; the alkanol is methanol, ethanol, iso-propanol or n-propanol; and the base in step (2) is sodium hydroxide or potassium hydroxide.

9. A process according to claim 7 wherein the catalyst complex is dihydridotetrakis(triphenylphosphine)ruthenium $(RuH_2(Ph_3P)_4)$, carbonylchlorohydridotris(triphenylphosphine)ruthenium $(RuClH(CO)(Ph_3P)_3)$, chlorohydridotris(triphenylphosphine)ruthenium $(RuHCl(Ph_3P)3)$, dichlorotris(triphenylphosphine)ruthenium $(RuCl_2(Ph_3P)_3)$, chlorotris(triphenylphosphine)rhodium $(RhCl(Ph_3P)_3)$, or hydridocarbonyltris(triphenylphosphine)rhodium $(RhH(CO)(Ph_3P)_3)$.

10. Process for the preparation of an aldehyde having the formula III

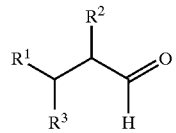

comprising the steps of:

(1) heating a reaction mixture comprising β,γ-ethylenically-unsaturated primary alcohol having the formula

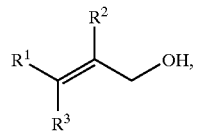

an alkanol of 1 to 3 carbon atoms, an acid, and a catalyst complex comprising at least one transition metal selected from ruthenium and rhodium, to obtain a dialkylacetal having the formula:

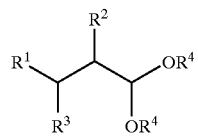

(2) adding a base to the reaction mixture of step (1);

(3) purifying the mixture resulting from step (2) to obtain a product comprising the dialkylacetal; and (4) contacting the dialkylacetal obtained in step (3) with an acid and water to obtain the aldehyde of formula III; wherein $R^1$, $R^2$, and $R^3$ are selected from hydrogen, branched or straight-chain $C_1$–$C_6$ substituted or unsubstituted alkyl, $C_6$–$C_{10}$ substituted or unsubstituted aryl, or $C_4$–$C_{10}$ substituted or unsubstituted heteroaryl, and $R^4$ is alkyl of 1 to 3 carbon atoms or the two $R^4$ groups in combination represent an alkylene.

11. Process according to claim 10 wherein the catalyst complex comprises at least one transition metal selected from ruthenium and rhodium and a phosphine having the formula:

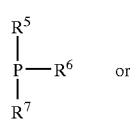

-continued

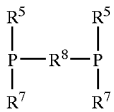
VI wherein $R^5$, $R^6$ and $R^7$ are the same or different and each is hydrocarbyl containing up to about 12 carbon atoms and $R^8$ is a hydrocarbylene linking group of 2 to 8 carbon atoms; the acid of step (1) is hydrochloric acid, sulfuric acid, a phosphoric acid, trifluoroacetic acid, or an alkyl- or aryl-sulfonic acids; the amount of alkanol employed in step (1) provides an alkanol: β,γ-ethylenically-unsaturated primary alcohol reactant weight ratio of about 3:1 to about 50:1; the base employed in step (2) is sodium or potassium hydroxide; and the acid employed in step (4) is acetic acid.

12. A process according to claim 11 wherein $R^1$ is phenyl and $R^2$ and $R^3$ are hydrogen.

13. A process according to claim 11 wherein the catalyst complex is dihydridotetrakis(triphenylphosphine)ruthenium ($RuH_2(Ph_3P)_4$), carbonylchlorohydridotris(triphenylphosphine)ruthenium ($RuClH(CO)(Ph_3P)_3$), chlorohydridotris(triphenylphosphine)ruthenium ($RuHCl(Ph_3P)_3$), dichlorotris(triphenylphosphine)ruthenium ($RuCl_2(Ph_3P)_3$), chlorotris(triphenylphosphine)rhodium ($RhCl(Ph_3P)_3$), or hydridocarbonyltris(triphenylphosphine)rhodium ($RhH(CO)(Ph_3P)_3$).

14. A process for the production of 4-phenyl-1-butyraldehyde, which comprises:
 (1) heating a reaction mixture comprising 4-phenyl-2-buten-1-ol, an alkanol having 1 to 3 carbon atoms, an acid, and a catalyst complex comprising at least one transition metal selected from ruthenium and rhodium, to obtain 4-phenyl-1,1-dialkoxybutane;
 (2) adding a base to the reaction mixture;
 (3) distilling the mixture from (2) to obtain a product comprising 4-phenyl-1,1-dialkoxybutane; and
 (4) adding water and an acid to the product of (3) to obtain 4-phenyl-1-butyraldehyde.

15. A process according to claim 14 wherein the alkanol is ethanol; the acid in (1) is hydrochloric acid, sulfuric acid, phosphoric acid, trifluoroacetic acid, benzenesulfonic, methanesulfonic or toluenesulfonic acid; the base is potassium hydroxide or sodium hydroxide; the acid in (4) is acetic acid; and the catalyst complex is dihydridotetrakis(triphenylphosphine)ruthenium ($RuH_2(Ph_3P)_4$), carbonylchlorohydridotris(triphenylphosphine)ruthenium ($RuClH(CO)(Ph_3P)_3$), chlorohydridotris(triphenylphosphine)ruthenium ($RuHCl(Ph_3P)_3$), dichlorotris(triphenylphosphine)ruthenium ($RuCl_2(Ph_3P)_3$), chlorotris(triphenylphosphine)rhodium ($RhCl(Ph_3P)_3$), or hydridocarbonyltris(triphenylphosphine)rhodium ($RhH(CO)(Ph_3P)_3$).

\* \* \* \* \*